United States Patent

Bosshart

[11] Patent Number: 5,858,417
[45] Date of Patent: Jan. 12, 1999

[54] RESIN INJECTOR WITH MUFFLE

[76] Inventor: Max Bosshart, Zurichstrasse 5 CH. 8440, Einsiedeln, Switzerland

[21] Appl. No.: 854,539

[22] Filed: May 12, 1997

[30] Foreign Application Priority Data

May 10, 1996 [ES] Spain ..................................... 9601060

[51] Int. Cl.⁶ .................................................. B29C 45/18
[52] U.S. Cl. .......................... 425/192 R; 249/54; 264/19; 425/562
[58] Field of Search ..................................... 425/186, 190, 425/192 R, 562, 542, 569, DIG. 11; 264/328.1, 19, 328.12; 249/54

[56] References Cited

U.S. PATENT DOCUMENTS

| 2,474,105 | 6/1949 | Hordes | 249/54 |
| 2,576,224 | 11/1951 | Hordes | 249/54 |
| 2,790,998 | 5/1957 | Dimmer | 425/DIG. 11 |
| 5,151,279 | 9/1992 | Kimura | 249/54 |
| 5,175,008 | 12/1992 | Ueno | 249/54 |
| 5,302,104 | 4/1994 | Ueda | 425/DIG. 11 |

FOREIGN PATENT DOCUMENTS 0370496  5/1990  European Pat. Off. .
0576744  1/1994  European Pat. Off. .

Primary Examiner—Patrick Ryan
Assistant Examiner—Joseph Leyson
Attorney, Agent, or Firm—Browdy and Neimark

[57] ABSTRACT

A resin injector is used to fill recesses created in plaster moulds containing teeth in the interior of muffles with resin, with a simple economic mechanical device which is attached to the muffle and is operated by a conventional press. An assembly of two cylindrical part (4,8) is adjusted to a wide inlet mouth cut in the muffle. The resin which is received in this assembly is projected towards the muffle through at least one hole, which can be opened or closed at will by means of a manually operated part.

7 Claims, 2 Drawing Sheets

RESIN INJECTOR WITH MUFFLE

FIELD OF THE INVENTION

The invention relates to a resin injector with a muffle, used in dental technology and intended for filling the interior of the muffles, in which the teeth and the mould are contained, with the said resin.

REVIEW OF THE RELATED TECHNOLOGY

To inject resin, the use of muffles of several varied shapes is known on the market, such as, for example, some composed of two half units connected to each other by bolts that pass through lugs—ad hoc—in each of the said halves.

To insert the resin, the muffles are provide with an upper hole, in which a special injector machine is situated, which, in combination with a press, inserts the resin into the interior of the mould, occupying the corresponding free spaces.

This traditional method of filling the moulds has a disadvantage in that it requires the use of a conventional injector, which is usually a costly part.

SUMMARY OF THE INVENTION

One object of the present invention is to provide a specially designed injector which is simple, easy to use and also has a low cost in comparison to traditional injecting machines.

Another object of the invention is to provide an injector which does not require the use of a flange to keep the muffle in position after injection, nor the use of a conventional injecting machine.

Another object of the invention is a muffle of the type which are composed of two hollow casings or bodies provided with devices to allow bolts to pass through, in which the hole in the upper casing is established with suitable dimensions for the insertion of one portion of the injector.

For the implementation and putting into practice of these objectives, the invention uses a conventional muffle composed of two halves, one of which has an open mouth to allow the resin to be inserted.

According to the invention, this inlet mouth is carried out in a generally circular shape with spacious dimensions as regards its diameter, of the order of between 40 and 150 millimeters, so as to allow the injector to be inserted.

The latter is composed basically of two complementary casings or bodies. One of these casings is of a hollow cylindrical shape with a straight generatrix (generating line), whose internal diameter is usually of some 80 millimeters, although it is claimed for exact operation in a range of between 40 and 150 millimeters. The Lower end of this cylindrical casing has a circular recess, in which the other casing of the injector, to be called base casing, is housed.

The base casing is a circular-shaped plate, not very high, provided with perimetral devices that correspond with the one in the assembly of the two half muffles, so that it is possible for the bolts that secure the base casing to the said half muffles to pass through.

This base casing also has a projecting circular edge on its upper face or surface, on which the lower part of the cylindrical casing is housed by the insertion of this circular edge into the lower recess in the said cylindrical casing.

The lower face of the base casing is provided with a cylindrical projection by way of a neck, which becomes housed in the central hole in the upper half muffle.

The base casing is also provided with a through central hole of an inverted trunco-conical shape, as well as one or more injection holes.

Moreover, the interiors of the two half muffles contain the moulds that include the teeth, as well as a resin inlet duct, which ensures that the gap or cavity between the said mould becomes occupied by the said resin.

In the front contact faces of the two half muffles, two radially positioned facing ducts are provided. These ducts have a semi-circular cross-section and extend from the exterior to the inner end of the resin inlet duct.

The two semicircular ducts form the housing for a central rod that has access from the exterior to the resin inlet duct.

The inner end of this rod is provided with a cut-out in the shape of a quarter of a sphere, simulating the end of a nib, cut just in the area of the rod that corresponds with the resin inlet duct, so that on turning the rod from the exterior in one direction, the entire part at its end closes the resin inlet duct, while on turning it in the opposite direction, the cut-out becomes aligned with the duct, allowing the resin to pass through into the interior of the muffles.

The hollow cylindrical casing of the injector forms an upwardly open chamber when it has been fitted to the upper edge of the base casing, so that the resin becomes housed in this chamber. On top of the resin and inside the chamber, a cylindrically-shaped part is provided by way of a piston, which is operated by the pin at the end of the screw-spindle of a conventional press.

On carrying out the movement of the screw-spindle of the press, the piston moves, exerting pressure on the resin in such a way that it is pushed through the trunco-conical central hole and through the off-centre hole, or at least through one of them if there are more than one.

The resin material that passes through the off-centre hole in the base casing enters into the resin inlet duct, allowing the internal space between the two half muffles to be filled until they are completely occupied.

In this operation, the previously mentioned rod is to be found in such a position that the end cut-out in its interior is aligned with the resin inlet duct, allowing the resin to flow through freely.

As a security measure and to prevent any possibility of the resin leaving its housing in the interior of the mould due to the effect of the overpressure that it might be submitted to, the rod is turned in such a way that its end cut-out changes position and the resin passage duct in the mould is closed.

The injector designed in accordance with the invention is easy and economic to build and also simple to use in application, with the lack of the use of any injecting machine nor flange whatsoever, given that the injector itself carries out these functions.

BRIEF DESCRIPTION OF THE DRAWING

All these and other details will be understood with greater clarity with reference to the accompanying sheets of drawings, in which the following are represented, with a non-restrictive nature.

DETAILED DESCRIPTION OF THE PREFERRED EMBODIMENT

Figure 1:
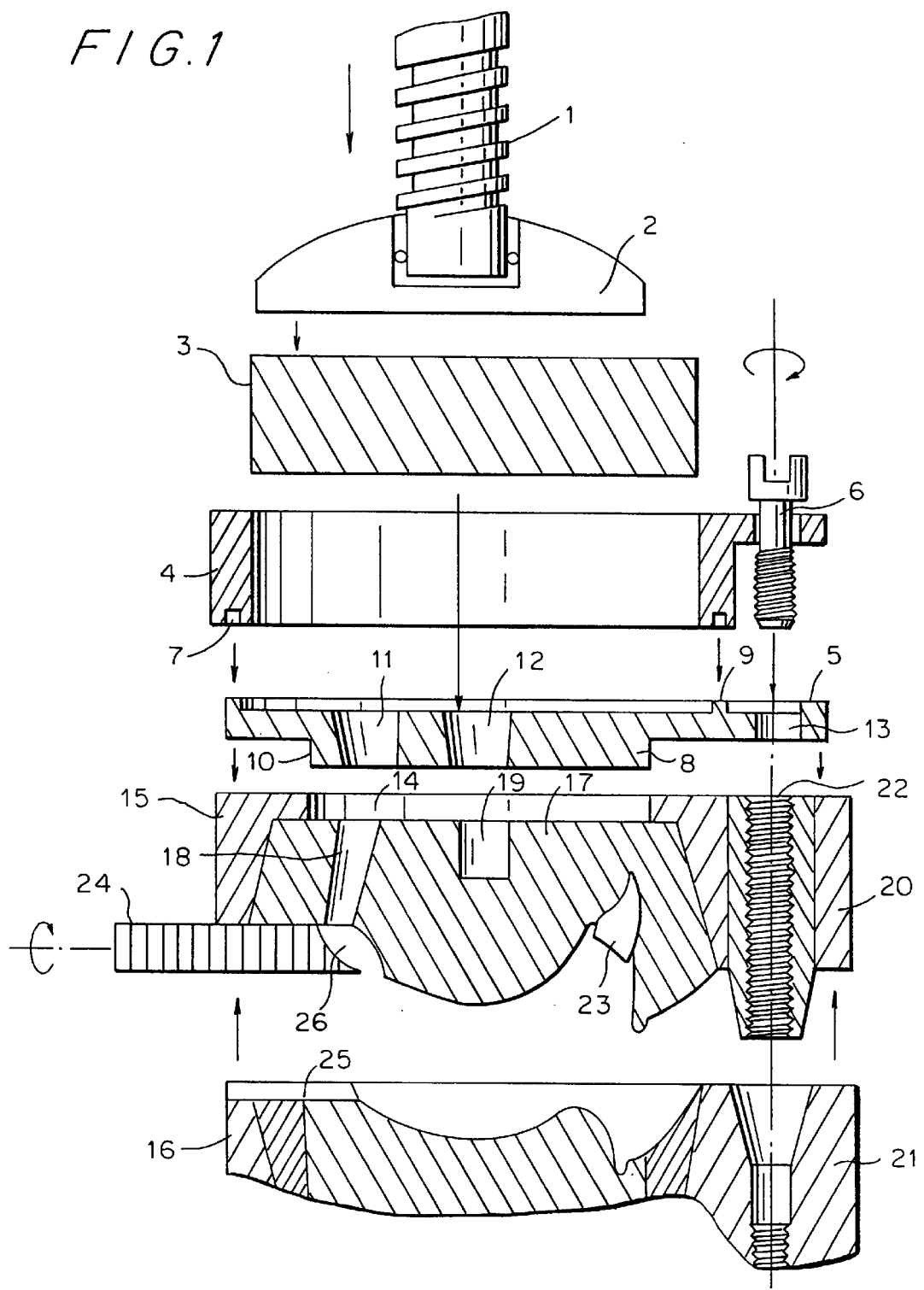
FIG. 1 shows a solution for the invention in a cross-section elevation of the injector assembly.

Looking now at FIG. 1, we can appreciate the screw-spindle (1) of the conventional press and its end or pusher plate (2), which is situated above the piston (3) of the injector, so that on turning the screw-spindle (1) in one direction, the pusher plate descends and exerts pressure on the piston (3).

The injector is made up of the hollow upper cylindrical part (4) and the base part (8), which are situated above the two half muffles (15,16), both provided with screw-threaded devices (20,21) in their interior (22) in order to facilitate the passage of the bolts (6). The cylindrical part (4) is preferably between 10 mm and 80 mm in height and between 40 mm and 150 mm in diameter.

In their interiors, these two half muffles (15,16) contain the moulds (17) which include the teeth (23), as well as the resin inlet duct (18) and the rod (24), by way of a nib at its inner end, that passes through slots (25) in both half muffles, cut in their contact areas.

The upper half muffle (15) has an upper hole or mouth (14), which will be between 40 and 150 millimeters in size, as been mentioned previously. The mouth (14) and lower neck (10) may be circular or non-circular in outline.

The two half slots (25) illustrated in this FIG. 1 can be composed of one single duct cut in the upper half muffle (15), a variant that is also considered to be covered by the invention, as well as any other practical solution intended for this purpose.

In the injector shown, the base casing (8) is provided with the lower projection (10) so that it can be housed in the cavity or recess (14) in the upper half muffle (15). In the same way, the trunco-conical central hole (12) is shown and the hole or holes (11) for the resin to pass through towards the duct (18) of the mould (17).

In the upper face of this base casing (8) appears the circular ledge (9) that determines the groove, from the base of which the holes (11) and (12) begin. The circular recess (7) of the cylindrical casing (4) becomes seated on this ledge (9).

In the solution illustrated in this FIG. 1, the base casing (8) is provided with the devices (5) provided with drill holes (13) to allow bolts (6) to pass through, which secure the casing to the half muffles.

The invention also covers the fact that the hollow cylindrical casing (4) can also be provided with similar devices drilled in harmony with those mentioned (5, 13), and even the fact that these devices with drill holes can be carried out only in the casing (4).

The particular arrangement of the rod (24) between the two half muffles (15,16) is perfectly visible in the context of FIG. 1. In the same way, we point out how its inner end is provided with a cut-out (26) which gives the end a shape similar to that of a nib. In the position illustrated, the duct (18) meets the cut-out (26), so that the resin is channelled through the said duct towards the cavity or gap in the prosthesis When the rod is turned 180 degrees from the exterior, its lower part closes the lower end of the duct, thus preventing the resin that is housed in the cavity of the prosthesis from reaching the exterior due to the effect of the overpressure generated.

Figure 2:
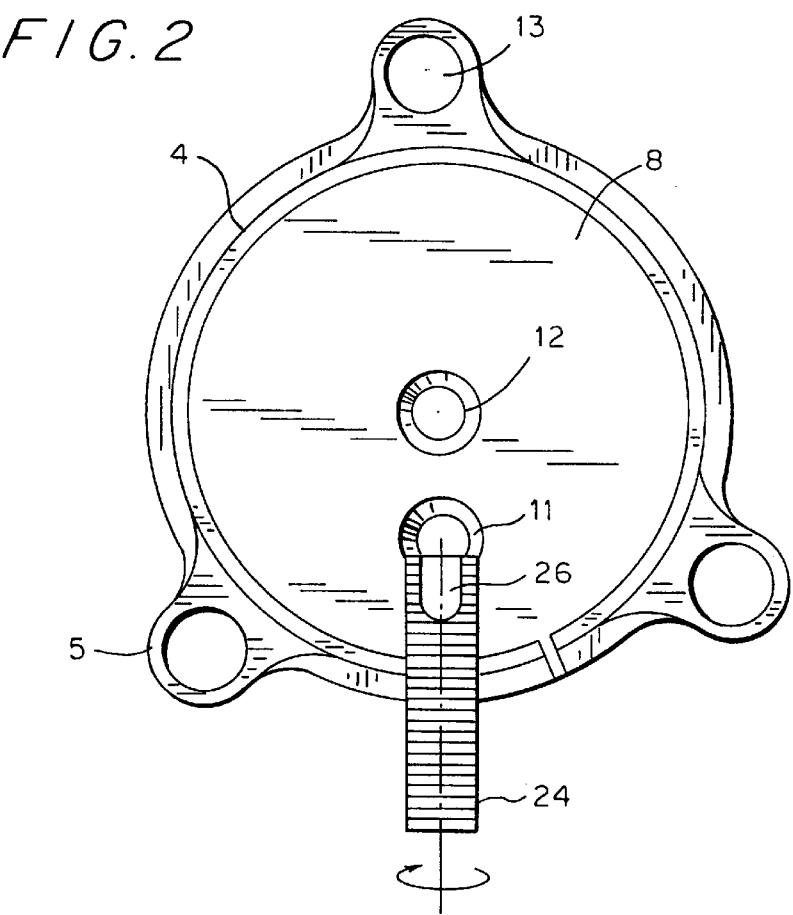
FIG. 2 is a top view of the above, from a horizontal line below the piston.

FIG. 2 allows us to appreciate the top view of the injector, with the hollow cylindrical casing (4) and the base casing (8), and with the devices (5) drill holed at (13) for the bolts to pass through. We can also observe the position of the centred trunco-conical hole (12) and of one of the holes (11) for the passage of the resin towards the duct (18), as well as the position of the rod (24). The hole (11) may be doubled and the two holes (11) arranged close to each other.

Figure 3:
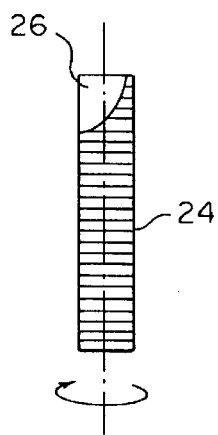
FIG. 3 is a view of the passage or closure rod of the mould resin duct.

FIG. 3 represents particularly the rod (24) with its end cut-out (26) in a concave shape in order to facilitate the passage or flow of the resin in the way described in relation to FIG. 1.

Figure 4:
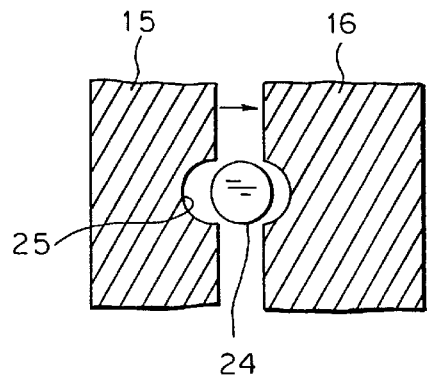
FIG. 4 is a detail that shows the situation of the rod in relation to the two half muffles.

Finally, with regard to FIG. 4, we can perfectly appreciate the two hemi-cylindrical grooves or half slots (25) in the fronts of both half muffles (15,16), between which the circular cross-section of the rod (24) is housed.

The operation of the injector is extremely simple, and begins with the arranging of the two half muffles (15, 16) containing the prosthesis (17), with the rod (24) being arranged in the slots (25) in the said half muffles, precisely in the position illustrated in FIG. 1. Next, the base part (8) is situated over the half muffle (15) and secured to it by means of the bolts (6).

The hollow cylindrical casing (4) is fitted onto the base casing, and the cavity in the casing (4) is filled with resin, with the piston (3) being arranged over the resin, after which the pusher plate (2) of the press is applied, being operated by means of the screw-spindle (1).

The pressure brought to bear by the pusher plate (2) on the piston (3) is transmitted to the resin, which passes through the hole (11) towards the duct (18) of the mould (17), filling up the cavity in the prosthesis. Once that the said cavity has been completely occupied or filled by the resin, the rod (24) is turned, so that it prevents the said resin from flowing out due to the overpressure created in the interior. The position of the rod, on turning it 180 degrees in relation to the position shown in FIG. 1, causes the closure of the duct (18).

It is important to point out, once having described the nature and advantages of this invention, its non-restrictive character, inasmuch as changes in the shape, materials or dimensions of its constituent parts will not in any way alter its essence, as long as they do not mean a substantial variation of the whole assembly.

What is claimed is:

1. A resin injector to be used with a press, the press having a pusher plate (2) at the end of a screw spindle (1); the resin injector comprising:

a muffle, the muffle further comprising two assembled half muffles (15,16);

a base casing (8) supported on an upper front part of the muffle;

a hollow generally cylindrical casing (4) supported on the base casing to create a resin receiving chamber;

the resin injector comprising a screw-thread device (5,13, 20,21) wherein connecting bolts (6) may be threaded to assemble the muffle, the base casing, and the cylindrical casing;

a generally cylindrical piston (3) slidable within the hollow cylindrical casing;

the base casing including a protruding lower neck (10) and the muffle comprising, in an upper portion thereof, a mouth (14) receiving therein the protruding lower neck of the base casing, wherein the base casing is supported on an upper front part of the muffle;

the mouth having a diameter of the order of between 40 and 150 millimeters;

the base casing (8) including on an upper face thereof a circular ledge (9), an inverted trunco-conical hole (12)

passing completely through the base casing, and at least one off-center hole (11) passing completely through the base casing and not centered, the off-center hole corresponding in position to a position of a resin inlet duct (18) cut in a mould portion (17) of the upper half muffle (15);

the circular ledge (9) of the base casing being received in an annular recess (7) in the hollow cylindrical casing (4);

whereby the piston (3), forced by the pusher plate (2) at the end of the screw spindle (1) of a press, forces resin through the off-center hole (11) towards the resin inlet duct (18);

contacting surfaces of the two half muffles each including a respective one of hemi-cylindrical grooves (25) extending, in a generally radial direction, into the resin inlet duct (18);

a rod (24) rotatably disposed within a cylindrical passage of the grooves when aligned, the rod being operable by turning from an exterior end and including an inner end at the resin inlet duct, the inner end including a cut-out (26) which has a nib shape, whereby the inner end opens and closes the resin inlet duct upon rotation thereof.

2. The resin injector according to claim 1, wherein the two assembled half muffles (15,16) include first screw-thread devices (20,21), and the base casing includes second screw-thread devices (5,13) corresponding with the first screw-thread devices of the half muffles, whereby the connecting bolts (6) housed in the first screw-thread devices between the half muffles are received in the second screw-thread devices.

3. The resin injector according to claim 2, wherein the hollow cylindrical casing (4) includes third screw-thread devices alignable with the first screw-thread devices and the second screw-thread devices.

4. The resin injector according to claim 1, wherein the two assembled half muffles (15,16) include first screw-thread devices (20,21), and the hollow cylindrical casing (4) includes third screw-thread devices alignable with the first screw-thread devices.

5. The resin injector according to claim 1, wherein the interior of the hollow cylindrical casing (4) has a height between 10 and 80 millimeters and a diameter between 40 and 150 millimeters.

6. The resin injector according to claim 1, wherein a transverse cross section of the lower neck (10) of the base casing (8) and the mouth (14) of the corresponding upper half muffle (15), are circular.

7. The resin injector according to claim 1, wherein a transverse cross section of the lower neck (10) of the base casing (8) and the mouth (14) of the corresponding upper half muffle (15), are non-circular.

* * * * *